United States Patent [19]

Bochis et al.

[11] Patent Number: 5,064,835
[45] Date of Patent: Nov. 12, 1991

[54] NEW HYDROXYMACROLIDE DERIVATIVES HAVING IMMUNOSUPPRESSIVE ACTIVITY

[75] Inventors: Richard J. Bochis, East Brunswick; Huyn O. Ok, Edison; Matthew J. Wyvratt, Mountainside, all of N.J.

[73] Assignee: Merck & Co., Inc., Rahway, N.J.

[21] Appl. No.: 486,700

[22] Filed: Mar. 1, 1990

[51] Int. Cl.$^5$ ............... A61K 31/395; A61K 31/695; C07D 498/16; C07F 7/01
[52] U.S. Cl. ..................................... 514/291; 514/63; 514/411; 540/452; 540/456
[58] Field of Search .................. 540/452, 456; 514/63, 514/291, 411

[56] References Cited

U.S. PATENT DOCUMENTS 4,894,366  1/1990  Okuhara et al. ............. 540/456

FOREIGN PATENT DOCUMENTS 0184162  6/1986  European Pat. Off. ............ 540/456
0315978  5/1989  European Pat. Off. ............ 540/456
0323042  7/1989  European Pat. Off. ............ 540/456

OTHER PUBLICATIONS

"Organic Chemistry", 3rd Ed. (1973) by Morrison and Boyd, pp. 590-591, 665-666 and 668-689.

Primary Examiner—Robert T. Bond
Attorney, Agent, or Firm—William H. Nicholson; Robert J. North; Raymond M. Speer

[57] ABSTRACT

Novel hydroxymacrolide derivatives of the general structural Formula I:

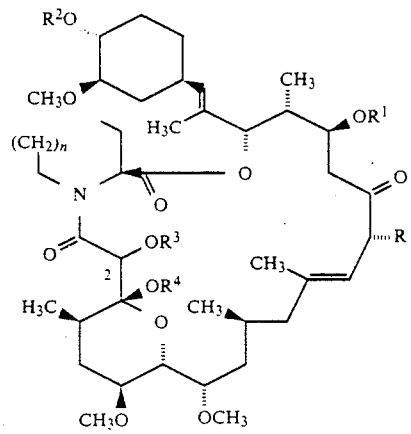

have been prepared from (a) suitable precursor(s) by selective reduction of the ketone at C-2. These macrolide immunosuppressants are useful in a human host for the treatment of autoimmune diseases (such as juvenile-onset diabetes melitus, multiple sclerosis and rheumatoid arthritis), infectious diseases and/or the prevention of rejection of foreign organ transplants, e.g. bone marrow and heart transplants.

In addition, these macrolide immunosuppressants are useful in the topical treatment of inflammatory and hyperproliferative skin diseases and cutaneous manifestations of immunologically-mediated illnesses such as: psoriasis, atopical dermatitiis, contact dermatitis and further eczematous dermatitises, seborrhoeic dermatitis. Lichen planus, Pemphigus, bullous Pemphigoid, Epidermolysis bullosa, urticaria, angioedemas, vasculitides, erythemas, cutaneous eospinphilias, Lupus erythematosus or Alopecia areata.

8 Claims, No Drawings

NEW HYDROXYMACROLIDE DERIVATIVES HAVING IMMUNOSUPPRESSIVE ACTIVITY

The present invention is related to compounds which are useful in a human host for the treatment of autoimmune diseases (such as juvenile-onset diabetes melitus, multiple sclerosis and rheumatoid arthritis), infectous diseases and/or the prevention of rejection of foreign organ transplants, e.g. bone marrow and heart transplants and are also useful in the topical treatment of inflammatory and hyperproliferative skin diseases and cutaneous manifestations of immunologically-mediated illnesses. More particularly, this invention relates to the selective reduction of the ketone at C-2 followed by acylation of compounds of the general structural Formula II:

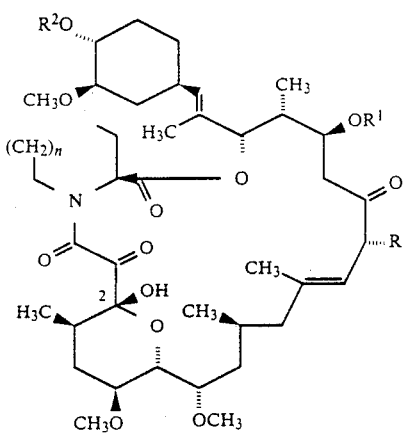

wherein:
R is methyl, ethyl, propyl, or allyl;
$R^1$ and $R^2$ are, independently, hydrogen or a hydroxyl protecting group; and
n is 1 or 2.

It also relates to pharmaceutical compositions containing the compounds and to a method of use of the present compounds and other agents for the treatment of autoimmune diseases, infectious diseases and/or the rejection of foreign organ transplants.

BRIEF DESCRIPTION OF DISCLOSURES IN THE ART

Fujisawa European and Japanese patents (EPO Publication No. 0,184,162 and PBJ Disclosure 63-17884) and publications (*J. Am. Chem. Soc.*, 1987, 109, 5031 and *J. Antibiotics*, 1987, 40, 1249) disclose 17-allyl-1,14--dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-2,3,10,16-tetraone (FR 900506), 17-ethyl 1,14 -dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (FR-900520) and related compound which are the starting materials for the preparation of the compounds described. The synthetic preparation of the aforementioned starting material (FR-900506) has recently been reported (*J. Am. Chem. Soc.*, 1989, 111, 1157). A Fisons European patent (EPO Publication No. 0,323,042) discloses various derivatives of FR 900506, FR-900520 and related compounds. A Sandoz European patent (EPO Publication No. 0,315,978) discloses the use of FR-900506 and related compounds in the topical treatment of inflammatory and hyperproliferative skin diseases and of cutaneous manifestations of immunologically-mediated illness.

BACKGROUND OF THE INVENTION

Immunoregulatory abnormalities have been shown to exist in a wide variety of "autoimmune" and chronic inflammatory diseases, including systemic lupus erythematosis, chronic rheumatoid arthritis, type 1 diabetes mellitus, inflammatory bowel disease, biliary cirrhosis, uveitis, multiple sclerosis and pemphigoid, sarcoidosis, psoriasis, ichthyosis, and other disorders such as Chrons disease, ulcerativ colitis, bullous Graves ophthalomopathy. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow or an organ transplantation, the host lymphocytes recognize the foreign tissue antigens and begin to produce antibodies which lead to graft rejection.

One end result of an autoimmune or a rejection process is tissue destruction caused by inflammatory cells and the mediators they release. Antiflammatory agents such as NSAID's and corticosteroids act principally by blocking the effect or secretion of these mediators but do nothing to modify the immunologic basis of the disease. On the other hand, cytotoxic agents such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

Cyclosporin A which was licensed by the U.S. FDA in 1983 is currently the leading drug used to prevent rejection of transplanted organs. The drug acts by inhibiting the body's immune system from mobilizing its vast arsenal of natural protecting agents to reject the transplant's foreign protein. Though cyclosporin A is effective in fighting transplant rejection, it is nephrotoxic and is known to cause several undesirable side effects including kidney failure, abnormal liver function and gastrointestinal discomfort.

Newer, safer drugs exhibiting less side effects are constantly being searched for in the field.

The 23-membered tricyclo-macrolide immunosuppressant, FR-900506,

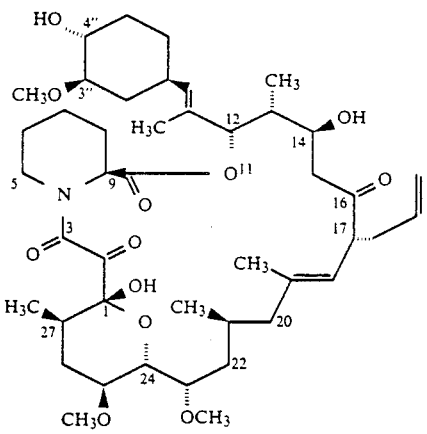

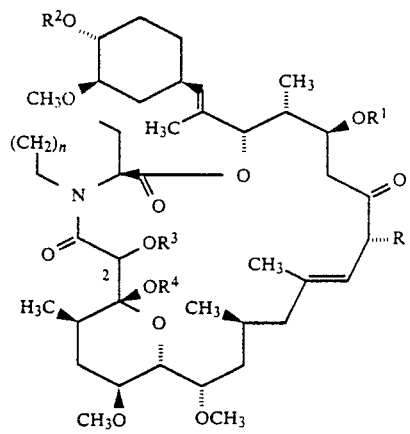

and related compound which were isolated and characterized by Tanaka, Kuroda, and co-workers at Fujisawa Pharmaceutical Co. in Japan, see *J. Am. Chem. Soc.*, 1987, 109, 5031, and EPO Pub. No. 0,184,162, have been shown to possess exceptional immunosuppressive activity. The compound FR-900506 has been reported to be 100 times more effective than cyclosporin in the suppression of in vitro immune systems (*J. Antibiotics* 1987, 40, 1256). In addition, these compounds are reputed to possess topical activity in the treatment of inflammatory and hyperproliferative skin diseases and cutaneous manifestations of immunologically-mediated illnessess (EPO Pub. No. 0,315,978).

Accordingly, an object of the present invention is to provide new analogs of these tricyclomacrolides which will (1) restore the balance of the help-and-suppression mechanism of the immune system by acting at an earlier point than the anti inflammatory agents and (2) induce specific long-term transplantation tolerance through a suppressor cell circuit without increasing the body's susceptibility to infection.

An additional object of the present invention is to provide analogs of these tricyclo-macrolides which possess topical activity in the treatment of inflammatory and hyperproliferative skin diseases and cutaneous manifestations of immunologically-mediated illnesses Another object of the present invention is to provide pharmaceutical compositions for administering to a patient in need of the treatment one or more of the active immunosuppressive agents of the present invention.

Still a further object of this invention is to provide a method of controlling graft rejection, autoimmune and chronic inflammatory diseases by administering a sufficient amount of one or more of the novel immunosuppressive agents in a mammalian species in need of such treatment.

Finally, it is the object of this invention to provide processes for the preparation of the active compounds of the present invention.

DETAILED DESCRIPTION OF THE INVENTION

SCOPE OF THE INVENTION

This invention relates to compounds of the general Formula I and pharmaceutically acceptable salts thereof:

wherein:

R is methyl, ethyl, propyl or allyl;

$R^1$ and $R^2$ are, independently, hydrogen, formyl, acetyl, propionyl or a hydroxyl protecting group;

$R^3$ is $C_1$-$C_6$ alkanoyl, preferably $R^3$ is formyl, acetyl or propionyl;

$R^4$ is hydrogen, formyl, acetyl or propionyl;

n is 1 or 2.

In the present invention, compounds with asymmetric centers may occur as racemates, racemic mixtures and as individual distereomers, with all isomeric forms of the compounds being included in the present invention.

As used herein, "alkanoyl" is intended to include those alkyl carbonyl groups of specified number of carbon atoms, which are exemplified by formyl, acetyl, propionyl and butyryl.

In the present invention it is preferred that in compounds of Formula I:

R is ethyl, propyl or allyl;

$R^1$ is hydrogen;

$R^2$ is hydrogen;

$R^3$ is formyl, acetyl or propionyl;

$R^4$ is hydrogen, formyl, acetyl or propionyl;

n is 1 or 2.

Prefered compounds of the present invention are compounds I, II, III, IV, V, VI, VII, and VIII as follows:

Compound I: 2-acetoxy-17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione;

Compound II: 2-acetoxy-17-ethyl-1,14-dihydroxy-1 2-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-3,10,16-trione;

Compound III: 2-acetoxy-17-propyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione;

Compound IV: 17-propyl-1,2-diacetoxy-14-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione;

Compound V: 17-propyl-2,14-diacetoxy-1-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo-[22.3.1.0$^{4,9}$]octacos-18-ene-3,10,16-trione;

Compound VI: 2-acetoxy-17-propyl-1,14-dihydroxy-12-[2'-(4''-acetoxy-3''methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione;

Compound VII: 17-propyl-2,14-diacetoxy-1-hydroxy-12-[2'-(4''-acetoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione;

Compound VIII: 17-propyl 1,2,14-triacetoxy-12-[2'-(4''acetoxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione.

PREPARATION OF COMPOUNDS WITHIN THE SCOPE OF THE PRESENT INVENTION

The starting materials for the preparation of the compounds of this invention are represented by Formula II:

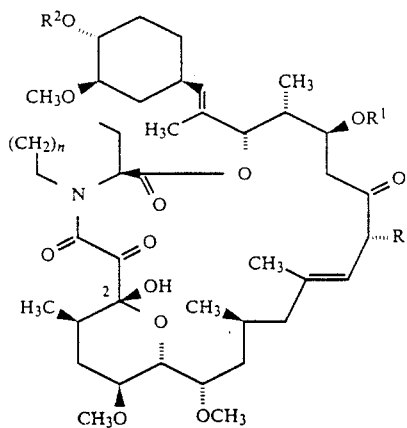

wherein:

R is methyl, ethyl, propyl or allyl, $R^1$ and $R^2$ are, independently, hydrogen or a hydroyl protecting group, and n is 1 or 2.

The production of compounds of Formula II is well known in the literature (see EPO Publication No. 0,184,162, PBJ Disclosure 63-17884; J. Am. Chem. Soc., 1987, 109, 5031 and J. Antibotics, 1987, 40, 1249). Both biological fermentation and synthetic processes may be found. A synthetic route to compounds of Formula II may be found in J. Am. Chem. Soc., 1989, 111, 1157.

Biological fermentation followed by synthetic modification is presently favored in the art as the method to produce compounds of Formula II. Organisms belonging to the genus Streptomyces such as Streptomyces tsukubaensis, No. 9993 and Streptomyces hygroscopicus, No. 7238 placed in an aqueous nutrient medium will produce desired compounds in isolable amounts. The nutrient medium contain sources of assimilable carbon and nitrogen, preferably under aerobic conditions. Produced in fermentation are four compounds of Formula II, (A) where: R is allyl, $R^1$ and $R^2$ are hydrogen, and n is 2; (B) where R is ethyl, $R^1$ and $R^2$ are hydrogen, and n is 2; (C) where R is methyl, $R^1$ and $R^2$ are hydrogen, and n is 2: and (D) where R is allyl, $R^1$ and $R^2$ are hydrogen, and n is 1.

A lyophilized sample of the isolated Streptomyces tsukubaensis, No. 9993 was deposited with the Fermentation Research Institute, Agency of Industrial Science and Technology (No. 1-3, Higashi 1-chome, Yatabemachi Tsukuba-gun, Ibaraki Prefecture, Japan) under the deposit number of FERM P-7886 (deposit date: Oct. 5th, 1984), and then converted to Budapest Treaty route of the same depository on Oct. 19, 1985 under the new deposit number of FERM BP-927.

Using the four compounds produced in fermentation above, the remaining compounds of Formula II may be easily produced. The allyl of R may be conveniently reduced to propyl by well known methods. The hydrogen of $R^1$ or $R^2$ may be protected by well known methods, for example as disclosed in EPO Publication 0,184,162.

Suitable protecting groups for hydroxyl include those groups well known in the art which are:

1-(lower alkylthio)(lower)alkyl wherein "lower alkyl" indicates a straight, cyclic or branched chain of one to six carbon atoms, such as lower alkylthiomethyl (e.g. methylthiomethyl, ethylthiomethyl, propylthiomethyl, isopropylthiomethyl, butylthiomethyl, isobutylthiomethyl, hexylthiomethyl, etc.), and the like, in which the preferred one may be $C_1$-$C_4$ alkylthiomethyl and the most preferred one may be methylthiomethyl; trisubstituted silyl such as tri(lower)alkylsilyl (e.g. trimethylsilyl, triethylsilyl, tributysilyl, tri-i-propylsilyl, tert-butyl-dimethylsilyl, tri-tert-butylsilyl, etc.), lower alkyldiarylsilyl (e.g. methyldiphenylsilyl, ethyl-diphenylsilyl, propyl-diphenylsilyl, tert-butyl-diphenylsily, etc.), and the like, in which the preferred one may be tri($C_1$-$C_4$) alkylsilyl and $C_1$-$C_4$ alkyl-diphenylsilyl, and the most preferred one may be tert-butyl-dimethylsilyl, tri-i-propylsilyl and tert-butyl-diphenylsilyl.

Compounds of Formula II, organisms to produce the same, conditions of fermentation, separation techniques, and chemical modification of the product are fully described in EPO Publication No. 0,184,162. This document is hereby incorporated by reference.

The compounds of the present invention which are represented by Formula I are prepared by the methods shown in the following Reaction Schemes wherein R, $R^1$, $R^2$, $R^3$, $R^4$, $R^5$ and n are as defined above unless otherwise indicated.

REACTION SCHEME A

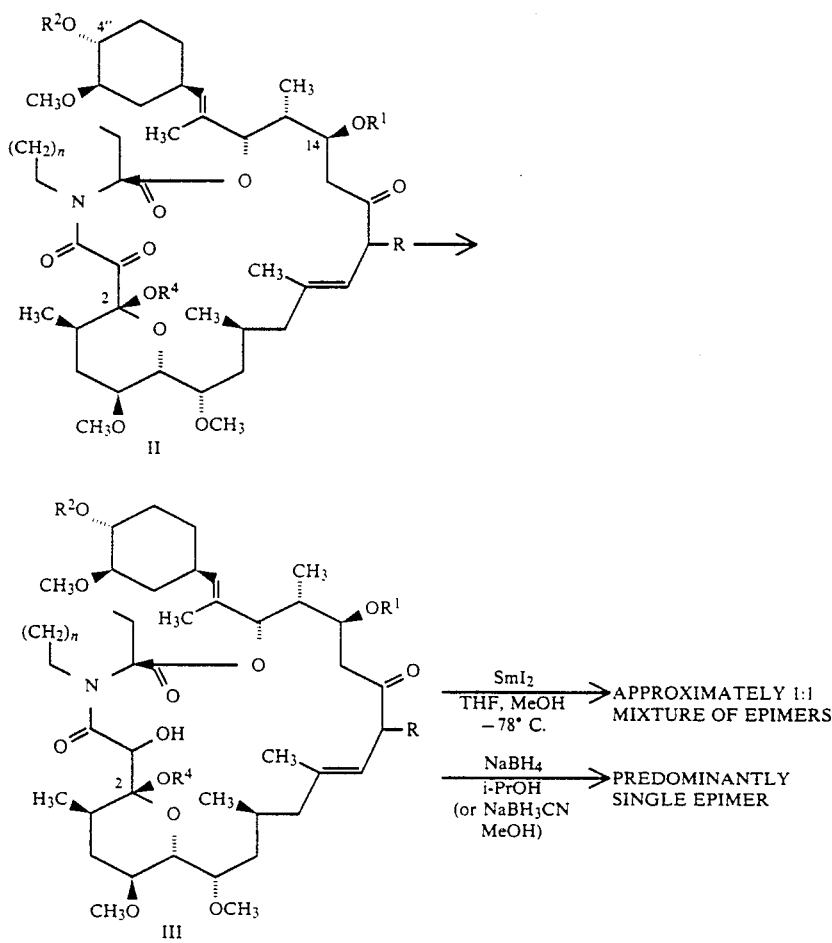

($R^1$ = OH
$R^2$ = H
$R^4$ = H
n = 2)

As shown in Reaction Scheme A the 1,14,4"-trihydroxy 2-ketomacrolide (II) is reduced with samarium iodide in the presence of methanol. Neutralization with saturated potassium carbonate gives a mixture of hydroxy macrolides (III) which are epimeric at C-2.

Alternatively, treatment of the 1,14,4"-trihydroxy 2-ketomacrolide (II) with sodium borohydride or sodium cyanoborohydride in an alcoholic solvent such as isopropanol followed by neutralization with cold acetic acid gives predominantly a single epimeric alcohol at C-2.

REACTION SCHEME B

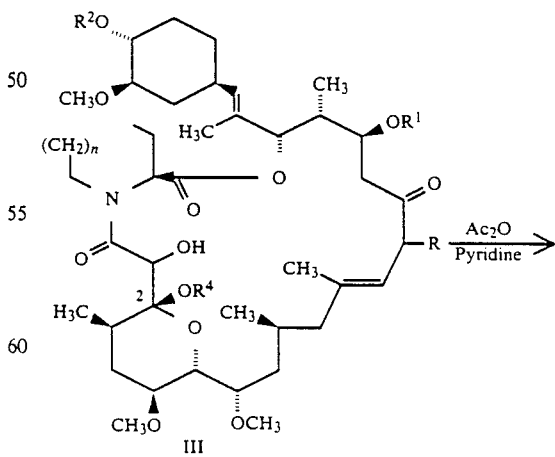

($R^1$ = H
$R^2$ = H
$R^4$ = H
n = 2)

-continued
REACTION SCHEME B

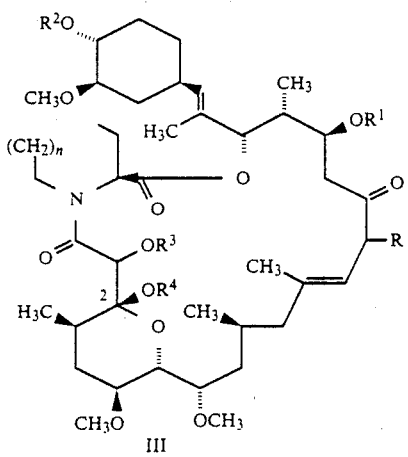

($R^1$ = H or acetyl
$R^2$ = H or acetyl
$R^3$ = acetyl
$R^4$ = H or acetyl
n = 2)

As shown in Reaction Scheme B the 1,2,14,4''-trihydroxy macrolide (III) is reacted with an acid anhydride (such as acetic anhydride) or an acid chloride (such as acetyl chloride) in a base (such as pyridine) to give a mixture of products acylated at C 2 and possibly acylated at C-1, C-14 and/or C-4''.

Similarly, the procedures described in Reaction Scheme A may be conducted utilizing the 1,14,3'',4''-tetrahydroxy macrolide (wherein $R^1$, $R^2$, and $R^4$ are hydrogen) to give the 1,2,14,3'',4''-pentahydroxymacrolide (wherein $R^1$, $R^2$, $R^3$ and $R^4$ are hydrogen). This product may then be acylated by the procedures described in Reaction Scheme B to give a mixture of acylated macrolides wherein $R^1$, $R^2$ and $R^4$ are, independently, hydrogen or acetyl and $R^3$ is acetyl.

Protection of the C-14, the C-3'' and/or the C-4'' hydroxyl group may be accomplished by methods known in the prior art for compounds of Formula II.

The object compounds of Formula I obtained according to the reactions as explained above can be isolated and purified in a conventional manner, for example, extraction, precipitation, fractional crystallization, recrystallization, chromatograpy, and the like.

It is to be noted that in the aforementioned reactions and the post treatment of the reaction mixture therein, the conformer and/or stereo isomer(s) of the object compounds of Formula I due to asymmetric carbon atom(s) or double bond(s) of the starting and object compounds may occasionally be transformed into the other conformer and/or stereoisomer(s), and such cases are also included within the scope of the present invention.

In the present invention, compounds with asymmetric centers may occur as racemates, racemic mixtures and as individual diastereomers, with all isomeric forms of the compounds being included in the present invention. These may be prepared by methods such as those disclosed in publications which describe synthetic routes to fragments of the macrolide FR-900506 and the total synthesis of the macrolide FR-900506 itself (*Tetrahedron Lett.*, 1988, 29, 277; *Tetrahedron Lett.*, 1988, 29, 281; *Tetrahedron Lett.*, 1988, 29, 4481; *J. Org. Chem.*, 1989, 54, 9; *J. Org. Chem.*, 1989, 54, 11; *J. Org. Chem.*, 1989, 54, 15; *J. Org. Chem.*, 1989, 54, 17; *J. Am. Chem. Soc.*, 1989, 111, 1157).

In addition compounds with carbon-carbon double bonds may occur in cis and trans form with all isomeric forms of the compounds being included in the present invention.

UTILITY OF THE COMPOUNDS WITHIN THE SCOPE OF THE INVENTION

The compounds of Formula I may be employed as immunosuppressants or antimicrobial compounds by methods and in dosages know in the prior art for compounds of Formula II. These compounds possess pharmacological activity such as imunosuppressive activity, antimicrobial activity, and the like, and therefore are useful for the treatment and prevention of the resistance to transplantation or transplantation rejection of organs or tissues such as heart, kidney, liver, medulla ossium, skin, etc., graft-versus-host diseases by medulla ossium transplantation, autoimmune diseases such as rheumatoid arthritis, systemic lupus erythematosis, Hashimoto's thyroiditis, multiple sclerosis, myasthenia gravis, type I diabetes, uveitis, etc., and infectious diseases caused by pathogenic microorganisms.

This invention also relates to a method of treatment for patients suffering from immunoregulatory abnormalities involving the administration of a compound of formula I as the active constituent.

For the treatment of these conditions and diseases caused by immmunoirregularity a compound of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixers. Compositions intended for oral use may be prepared according to any method known to the art for the manufacture of pharmaceutical compositions and such compositions may contain one or more agents selected from the group consisting of a sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by know techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874 to form osmotic therapeutic tablets for controlled release.

In some cases, formulations for oral use may be in the form of hard gelation capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
  (1) suspending agents such as sodium carboxymethylcellulose, methylcellulose, hydroxypropylmethylcellulose, sodium alginate, polyvinylpyrrolidone, gum tragacanth and gum acacia;
  (2) dispersing or wetting agents which may be
    (a) a naturally-occurring phosphatide such as lecithin,
    (b) a condensation product of an alkylene oxide with a fatty acid, for example, polyoxyethylene stearate,
    (c) a condensation product of an ethylene oxide with a long chain aliphatic alcohol, for example, heptadecaethyleneoxycetanol,
    (d) a condensation product of ethylene oxide with a partial ester derived from a fatty acid and a hexitol such as polyoxyethylene sorbital monooleate, or
    (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents and flavoring agents may be added to provide a palatable oral preparation. These compositions may be prepared by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil in-water emulsions. The oily phase may be a vegetable oil such as olive oil or arachis oils, or a mineral oil such as liquid paraffin or a mixture thereof. Suitable emulsifying agents may be (1) naturally, occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A compound of formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the immunoregulants are employed.

Dosage levels of the order from about 0.5 mg to about 100 mg per kilogram of body weight per day are useful in the treatment of the above-indicated conditions (from about 25 mg to about 5 gm per patient per day). In addition, the compounds of the present invention may be administered on an intermittent basis; i.e. at semiweekly, weekly, semimonthly or monthly intervals.

The amount of active ingredient that may be combined with the carrier materials to produce a single dosage form will vary depending upon the host treated and the particular mode of administration. For example, a formulation intended for the oral administration of humans may contain from 0.5 mg to 5 gm of active agent compounded with an appropriate and convenient amount of carrier material which may vary from about 5 to about 95 percent of the total composition. Dosage unit forms will generally contain from about 0.5 mg to about 500 mg of active ingredient.

It will be understood, however, that the specific dose level for any particular patient will depend on upon a variety of factors including the activity of the specific compound employed, the age, body weight, general health, sex, diet, time of administration, route of administration, rate of excretion, drug combination and the severity of the particular disease undergoing therapy.

The following examples are given for the purpose of illustrating the present invention and shall not be construed as being limitations on the scope or spirit of the instant invention.

EXAMPLE 1

7-Allyl-1,2,14-trihydroxy-12-[2'-(4''-hydroxy-3''-methoxycyclohexyl)-1'-methylvinyl]-23,25-dimethoxy-13,19,21,27-tetramethyl-11,28-dioxa-4-aza-tricyclo[22.3.1.0$^{4,9}$]octacos-18-ene-3.10.16-trione Samarium (63 mg, 0.42 μmol) was placed in a flame dried 10 ml round bottomed flask and 1 ml of dry THF was added under nitrogen. A solution of 1,2-diiodoethane (56 mg, 0.4 μmol) in 1 ml of dry THF was added dropwise at RT and stirred for one hour (color of reaction changed from clear to dark blue). The dark blue solution was cooled to −78° C. (dry ice/acetone bath) and a solution of 17-allyl-1,14-dihydroxy-12-[2-40 -(4''-hydroxy-3''-methoxycyclohexyl)-1-'-methylvinyl]-23,25-dimethoxy-13,19,21,27-tetramethyl-11,28-dioxa-4-azatricyclo[22.3.1.0$^{4,9}$]octacos-18-ene-3,10,16-tetraone (100 mg) in 3 ml THF:MeOH (50:50) was added dropwise (color of reaction mixture changed from dark blue to light green). Reaction mixture was stirred for 20 minutes at −78° C. and then temperature was raised to RT. Reaction mixture was poured into sat. K$_2$CO$_3$ and extracted with ethyl acetate (3×30 ml). Combined organic layers were washed with water and brine and dried over MgSO$_4$. Evaporation of solvent gave 140 mg of crude product which was purified by prep TLC (10% i-PrOH/CH$_2$Cl$_2$) to give 12 mg (of the title compound (with NMR and mass spectra consistent with the structure).

Mass spectrum:m/e=805 (M+).

EXAMPLE 2

17-Allyl-1,2,14-trihydroxy 12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,-16-trione (Alternate Route)

To a stirred solution of 17-allyl -1,14-dihydroxy-12-[2'-(4''-hydroxy-3''-methoxycyclohexyl)1-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (300 mg, 0.374 mmol) in 9 ml MeOH was added dropwise at RT a solution of NaBH$_4$ (0.12 mmol) in 2 ml isopropanol. After stirring at RT for 15 minutes the reaction was quenched by pouring into 1.5 ml acetic acid in ice and the mixture was extracted with ethyl acetate (3×50 ml). The combined organic layers were washed with sat. NaHCO$_3$ (1×50 ml) and water (1×50 ml) and dried over MgSO$_4$. Evaporation of solvent gave 320 mg of crude product which was purified by prep TLC (10% i-PrOH/CH$_2$Cl$_2$) to give 127 mg (42% yield) of the title compound (with NMR and mass spectra consistent with the structure).

EXAMPLE 3

17-Allyl-1,2,14-trihydroxy-12-[2'-(4''-hydroxy-3''-methoxycyclohexyl)-1'methylvinyl]-23,25-dimethoxy-13,19,21,27-tetramethyl-11,28-dioxa-4-azatricyclo[22.3.1.0$^{4,9}$]octacos-18-ene-3,10,16-trione (Alternate Route)

To a stirred solution of 17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-2,3,10,16-tetraone (108 mg, 0.135 mmol) in 4 ml MeOH cooled to −5° C. (ice/acetone bath) was added in several portions NaBH$_3$CN (160 mg). After addition was complete reaction was allowed to warm to RT. After stirring at RT for 2 hours the reaction mixture was diluted with 10 ml CH$_2$Cl$_2$ and purified by prep TLC (5% MeOH/CH$_2$Cl$_2$) to give the title compound (with NMR and mass spectra consistent with the structure).

EXAMPLE 4

Peracetylation of 17-Allyl-1,2,14-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3-3,10,16-trione To a stirred solution of 17-allyl-1,2,14-trihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione (20 mg, 25 μmol) in 100 μl of dry pyridine was added a large excess (100 μl ) of freshly distilled acetic anhydride under nitrogen atmosphere. The reaction mixture was stirred at r.t. for 4.5 hours by which time most of the starting material had disappeared. Remaining reagents were removed under a stream of nitrogen and the yellow residue was purified by prep TLC (Silica Gel 500 microns, 6:4 ethyl acetate:hexane, multiple elution) to give 8 mg of 17-ally-1,2,14-triacetoxy-12-[2'-(4''-acetoxy-3''-methoxycyclohexyl)-1'-methylvinyl]-23,25-dimethoxy-13,19,21,27-tetramethyl 11,28-dioxa-4-aza-tricyclo[22.3.1.0$^{4,9}$]octacos-18-ene-3,10.16-trione, 3 mg of 17-allyl-2,14-diacetoxy-1-hydroxy-12-[2'(4''-acetoxy-3''-methoxycyclohexyl)1'-methylvinyl]-23,25-dimethoxy-13,19,21,27-tetramethyl-11,28-dioxa-4-aza-tricyclo[22.3.1.0$^{4,9}$]octacos-18-ene-3,10,16-trione, 3 mg of 17-allyl-1,14-diacetoxy-2-hydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione, and 5 mg of 14-acetoxy-17-allyl-1,2-dihydroxy-12-[2'-(4''-acetoxy-3''-methoxycyclohexyl)-1'-methylvinyl]-23,25-dimethoxy-13,19,21,27-tetramethyl-11,28-dioxa-4-azatricylo[22.3.1.0$^{4,9}$]octacos-18-ene-3,10,16-trione (NMR and mass spectra consistent with the above structures.)

EXAMPLE 5

2-Acetoxy-17-allyl-1,14-dihydroxy-12-[2'-(4''-hydroxy-3''-methoxycyclohexyl)-1'-methylvinyl]-23,25-dimethoxy-13,19,21,27-tetramethyl-11,28-dioxa-4-azatricyclo[22.3.1.0$^{4,9}$]octacos-18-ene-3,10,16-trione Step A: Preparation of 17-Allyl-1-hydroxy-12-2'-4''-triisopropylsilyoxy-3'-methoxycyclohexyl)-1'-methylvinyl]-14-triisopropylsilyoxy-23,25-dimethoxy-13,19,21,27-tetramethyl-11,28-dioxa-4-azatricyclo[22.3.1.$^{4,9}$]octacos-18-ene-2,3,10,16-tetraone To a cooled solution (0° C.) of 17-allyl-1,14-dihydroxy-12-[2'-(4''-hydroxy-3''-methoxycyclohexyl)-1'-methylvinyl]23,25-dimethoxy-13,19,21,27-tetramethyl-11,28-dioxa-4-azatricyclo[22.3.1.0$^{4,9}$]-octacos-18-ene-2,3,10,16-tetraone (120 mg) in dry methylene chloride (15 ml) is added 2,6-lutidine (64.3 mg) followed by triisopropylsilyl trifluoromethanesulfonate (184 mg). Reaction temperature is raised to r.t. and stirred overnight under nitrogen atmosphere. The reaction is quenched with 10 ml of water and extracted with ethyl acetate. Organic layer is washed (water, sat'd NaHCO$_3$, sat'd NaCl) and dried (anhydrous MgSO$_4$). Removal of solvent followed by chromatography on silica gel (70% hexane/ethyl acetate) gives the title compound.

Step B: Preparation of 17-Allyl-1,2-dihydroxy-12-[2'-(4"-triisopropylsilyoxy-3"-methoxycyclohexyl)-1'-methylvinyl]-14-triisopropylsilyoxy-23,25-dimethoxy-13,19,21,27-tetra-methyl-11,28-dioxa-4-azatricyclo[22.3.1.0^{4,9}]octacos-18-ene-3,10,16-trione The title compound is prepared from 17-allyl-1-hydroxy-12-[2'-(4"-triisopropylsilyoxy-3"-methoxycyclohexyl)-1'-methylvinyl]-14-triisopropylsilyloxy-23,25-dimethoxy-13,19,21,27-tetramethyl-11,28-dioxa-4-azatricyclo[22.3.1.0^{4,9}]octacos-18-ene-2,3,-10,16-tetraone utilizing the method of Example 1 or Example 2.

Step C: Preparation of 2-Acetoxy-17-allyl-1-hydroxy-12-[2'-(4"-triisopropylsilyoxy-3"-methoxycyclohexyl)-1'-methylvinyl]-14-triisopropyl-silyloxy-23,25-dimethoxy-13,19,21,27-tetramethyl-11,28-dioxa-4-azatricyclo[22.3.1.0^{4,9}]octacos-18-ene-3,10,16-trione and 1-Acetoxy-17-allyl-2-hydroxy-12-[2'-(4"-triisopropylsilyloxy-3"-methoxycyclo-hexyl)-1'-methylvinyl]-14-triisopropylsilyoxy-23,25-dimethoxy-13,19,21,27-tetramethyl-11,28 dioxa-4-azatricyclo[22.3.1.0^{4,9}]octacos-18-ene-3,10,16-trione A mixture of the title compounds is prepared from 17-allyl-1,2-dihydroxy-12-[2'-(4"-triisopropylsilyloxy-3"-methoxycyclohexyl)-1'-methylvinyl]-14-triisopropylsilyloxy-23,25-dimethoxy-13,19,21,27-tetramethyl-11,28-dioxa-4-azatricyclo[22.3.1.0^{4,9}]-octacos-18-ene-3,10,16-trione utilizing the method of Example 4.

Step D: Preparation of 2-Acetoxy-17-allyl-1,14-dihydroxy-12-[2'-(4"-hydroxy-3"-methoxycyclohexyl)-1'-methylvinyl]-23,25-dimethoxy-13,19,21,27-tetramethyl-11,28-dioxa-4-azatricyclo[22.3.1.0^{4,9}]octacos-18-ene-3,10,16-trione To a solution of 2-acetoxy-17-allyl-1-hydroxy-12-[2'-(4"-triisopropylsilyloxy-3"-methoxycyclohexyl)-1'-]-14-triisopropylsilyloxy-23,25-dimethoxy-13,19,21,27-tetramethyl-11,28-dioxa-4-azatricyclo-[22.3.1.0^{4,9}]octacos-18ene-3,10,16-trione and 1-acetoxy-17-allyl-2-hydroxy-12-[2'-(4"-triisopropylsilyloxy-3"-methoxycyclohexyl)-1'-methylvinyl]-14-triisopropylsilyoxy-23,25-dimethoxy-13,19,21,27-tetramethyl-11,28-dioxa-4-azatricyclo[22.3.1.0^{4,9}]octacos-18-ene-3,10,16-trione-(10 m) in acetonitrile (1 ml) is added 0.2 ml of hydrogen fluoride (48%) at room temperature. The reaction mixture is stirred for 6 hours, quenched with aqueous sodium bicarbonate and extracted with ethyl acetate. Removal of solvent, followed by chromatography on silica gel (5% i-ProH/CH2Cl2) and HPLC gives the title compound.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents

What is claimed is:

1. A compound of formula I:

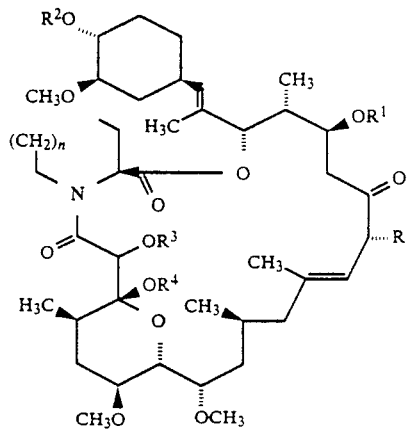

wherein:
R is methyl, ethyl, propyl or allyl;
$R^1$ and $R^2$ are, independently, hydrogen, formyl, acetyl, or propionyl;
$R^3$ is $C_1$-$C_6$ alkanoyl,
$R^4$ is hydrogen, formyl, acetyl or propionyl;
n is 1 or 2;
or the pharmaceutically acceptable salt thereof.

2. The compound of claim 1 wherein:
R is methyl, ethyl, propyl or allyl:
$R^1$ is hydrogen;
$R^2$ is hydrogen;
$R^3$ is $C_1$-$C_6$ alkanoyl;
$R^4$ is hydrogen, formyl or acetyl;
n is 1 or 2;
or the pharmaceutically acceptable salt thereof.

3. The compound of claim 2 wherein:
R is methyl, ethyl, propyl or allyl,
$R^1$ is hydrogen;
$R^2$ is hydrogen:
$R^3$ is formyl or acetyl;
$R^4$ is hydrogen, formyl or acetyl;
n is 1 or 2;
or the pharmaceutically acceptable salt thereof.

4. The compound according to claim 1, selected from the group consisting of compounds of the formula I wherein:
(a) R is allyl, $R^1$ is hydrogen, $R^2$ is hydrogen, $R^3$ is acetyl, $R^4$ is hydrogen and n is 2;
(b) R is ethyl, $R^1$ is hydrogen, $R^2$ is hydrogen, $R^3$ is acetyl, $R^4$ is hydrogen and n is 2;
(c) R is propyl, $R^1$ is hydrogen, $R^2$ is hydrogen, $R^3$ is acetyl, $R^4$ is hydrogen and n is 2;
(d) R is allyl, $R^1$ is hydrogen, $R^2$ is hydrogen, $R^3$ is acetyl, $R^4$ is hydrogen and n is 1,
(e) R is ethyl, $R^1$ is hydrogen, $R^2$ is hydrogen, $R^3$ is acetyl, $R^4$ is acetyl and n is 2;
(f) R is ethyl, $R^1$ is acetyl, $R^2$ is hydrogen, $R^3$ is acetyl, $R^4$ is hydrogen and n is 2;
(g) R is ethyl, $R^1$ is hydrogen, $R^2$ is acetyl, $R^3$ is acetyl, $R^4$ is hydrogen and n is 2;
(h) R is ethyl, $R^1$ is acetyl, $R^2$ is acetyl, $R^3$ is acetyl, $R^4$ is hydrogen and n is 2;
(i) R is ethyl, $R^1$ is acetyl, $R^2$ is acetyl, $R^3$ is acetyl, $R^4$ is acetyl and n is 2.

5. A pharmaceutical composition for the treatment of immunoregulatory disorders or diseases comprising a pharmaceutical carrier and a therapeutically effective amount of the compound of formula I, according to claim 1.

6. A pharmaceutical composition for the topical treatment of inflammatory and hyperproliferative skin diseases and or cutaneous manifestations of immunologically-medicated illnesses comprising a pharmaceutical carrier and a therapeutically effective amount of the compound of formula I, according to claim 1.

7. A method for the treatment of immunoregulatory disorders or diseases comprising the administration to mammalian species in need of such treatment of an effective amount of the compound of formula I according to claim 1.

8. A method for the topical treatment of inflammatory and hyperproliferative skin diseases and or cutaneous manifestations of immunologically-medicated illnesses comprising the administration to a mammalian species in need of such treatment of an effective amount of the compound of formula I according to claim 1.

* * * * *